(12) United States Patent
Zhang et al.

(10) Patent No.: US 11,844,883 B2
(45) Date of Patent: Dec. 19, 2023

(54) DISINFECTING FLUID USING DISINFECTION LIGHT

(71) Applicant: Bolb Inc., Livermore, CA (US)

(72) Inventors: Jianping Zhang, Arcadia, CA (US); Huazhong Deng, Guangdong (CN); Bin Zhang, Pleasanton, CA (US); Ling Zhou, Dublin, CA (US); Ying Gao, Fremont, CA (US)

(73) Assignee: BOLB INC., Livermore, CA (US)

( * ) Notice: Subject to any disclaimer, the term of this patent is extended or adjusted under 35 U.S.C. 154(b) by 0 days.

(21) Appl. No.: 17/740,282

(22) Filed: May 9, 2022

(65) Prior Publication Data

US 2022/0265886 A1 Aug. 25, 2022

Related U.S. Application Data

(62) Division of application No. 16/842,760, filed on Apr. 8, 2020, now Pat. No. 11,364,316.

(51) Int. Cl.
*A61L 9/16* (2006.01)
*A61L 9/12* (2006.01)

(52) U.S. Cl.
CPC ............... *A61L 9/122* (2013.01); *A61L 9/16* (2013.01); *A61L 2202/121* (2013.01); *A61L 2209/11* (2013.01); *A61L 2209/12* (2013.01); *A61L 2209/14* (2013.01)

(58) Field of Classification Search
CPC ..... A61L 9/16; A61L 9/18; A61L 9/20; A61L 9/205; A61L 2209/121; A61L 2209/122; A61L 2209/11; A61L 2209/12; A61L 2209/14
See application file for complete search history.

(56) References Cited

U.S. PATENT DOCUMENTS

| | | | |
|---|---|---|---|
| 6,337,483 B1 * | 1/2002 | Matschke | A61L 9/20 250/435 |
| 8,017,073 B2 * | 9/2011 | Engelhard | A61L 9/00 422/24 |
| 2007/0163588 A1 * | 7/2007 | Hebrank | A61M 16/0069 128/205.29 |

* cited by examiner

*Primary Examiner* — Timothy C Cleveland
(74) *Attorney, Agent, or Firm* — J.C. PATENTS

(57) ABSTRACT

An air disinfection device includes: a housing that includes an inlet port for taking air therethrough and a disinfection chamber that has a shell in a shape of a truncated ellipsoid. The device also includes: a disinfection head that is disposed in the inlet port and includes a light source for generating disinfection light that disinfects the air in the disinfection chamber, where the light source is located substantially on a plane where a first focal point of the truncated ellipsoid is located. The disinfection head further includes a fan for taking the air through the inlet port to the disinfection chamber and a filter for filtering the air. The device further includes a power source electrically coupled to the disinfection head and configured to provide electrical power for the disinfection head.

11 Claims, 13 Drawing Sheets

DISINFECTING FLUID USING DISINFECTION LIGHT

CROSS-REFERENCE TO PRIOR APPLICATIONS

This application is a divisional application of a U.S. patent application Ser. No. 16/842,760, filed on Apr. 8, 2020, which is hereby incorporated by reference in its entirety.

BACKGROUND

A. Technical Field

The present invention relates to devices for disinfecting fluid, and more particularly, to air disinfection apparatus using disinfection light.

B. Background of the Invention

Air under circumstances may carry infectious pathogenic microorganisms, such as bacteria, spores, viruses, and fungi, that need to be disinfected/sterilized to protect public health. For instance, COVID-19, like the flu, can be spread from person to person and throughout the community very quickly. When a person infected with COVID-19 viruses coughs, sneezes or talks, the viruses can be spread over a short distance by the breath droplets either floating in air or settled down on surrounding surfaces. Then, a healthy person may get infected by the virus if the person inhales the droplets, touches those surfaces or objects and then touches his/her mouth, nose or eyes.

Physicians and healthcare providers, who provide care for epidemic/pandemic patients, may be exposed to high risk of infection unless they wear proper protection equipment to safeguard against the contaminated air. One type of equipment may be a self-contained breathing apparatus (SCBA). FIG. 1 shows a conventional SCBA 100. As depicted, the SCBA 100 contains a high-pressure gas tank for storing uncontaminated air, a pressure regulator, and an inhalation connection (mouthpiece and a face mask). Even though the SCBA 100 is not dependent on a remote air supply, it has several drawbacks: (i) the gas tank is heavy and bulky; (ii) the air flow lasts only a few tens of minutes (e.g., 10-30 minutes), causing the gas tank to be refilled or replaced frequently; and (iii) the SCBA is extremely expensive. For these reasons, the SCBA 100 may be suitable for firefighters, but not for the physicians who need to provide healthcare services for several hours per day.

Another type of equipment may be a powered, air-purifying respirator (PAPR). FIG. 2 shows a conventional PAPR 200, which is a personal protective equipment used to safeguard the user against contaminated air. Typically, the PAPR includes: a head gear (mask or hood) 202; an air supply unit 206; and a hose 204 connected to the head gear and air supply unit. The air supply unit 206 takes ambient air that is contaminated with one or more type of pollutant or pathogenic microorganisms, removes (filters) a sufficient proportion of these contaminations, and then delivers the clean air to the head gear 202 through the hose 204.

Compared to the SCBA 100, the PAPR 200 has a few advantages: less weight, less manufacturing cost, and less effort for maintenance, i.e., the filter needs to be replaced less frequently than the gas tank. For these reasons, the PAPR 200 is currently used by physicians who provide medical services for epidemic/pandemic patients. However, the PAPR 200 also has several drawbacks: (i) the PAPR has the filtration function only; and (ii) the PAPR is not able to disinfect germs (such as viruses of submicron sizes) that pass through the filter, i.e., the PAPR 200 is ineffective in airborne contaminant removal. Thus, the PAPR 200 is not an ideal equipment for epidemic/pandemic events, even though it is currently used by physicians.

As such, there is a need for equipment for epidemic/pandemic events, which can provide disinfected and uncontaminated air for health providers and patients without compromising the weight, manufacture cost and effort for the maintenance.

SUMMARY OF THE DISCLOSURE

In one aspect of the present invention, an air disinfection device includes: a housing having an inlet port and a disinfection chamber that has a shape of a first frustum; and a disinfection head disposed in the inlet port and including a fan for taking air into the housing, a filter for filtering the air; and a light source for generating disinfection light that forms a second frustum of light and disinfects the air in the disinfection chamber. The air disinfection device further includes a power source that provides electrical power for the disinfection head. The light source is arranged so that a lateral surface of the second frustum of light is substantially identical to an inner lateral surface of the disinfection chamber. Also, the light source is disposed near a top of the first frustum so that an entire portion of a space defined by the disinfection chamber is located within the second frustum of light.

In another aspect of the present invention, an air disinfection device includes: a housing having an inlet port and a disinfection chamber that includes a shell in the shape of a truncated ellipsoid; and a disinfection head disposed in the inlet port and including a fan for taking air into the housing, a filter for filtering the air; and a light source for generating disinfection light that disinfects the air in the disinfection chamber. The light source is located substantially on a focus of the truncated ellipsoid. The air disinfection device further includes a power source that provides electrical power for the disinfection head.

In another aspect of the present invention, an air disinfection device includes: a housing having an inlet port for receiving air; a disinfection chamber having a shape that includes first and second frusta, the air being disinfected in the disinfection chamber; and an outlet port through which the air exits. The air disinfection device further includes: a light source disposed in the inlet port and configured to generate disinfection light that forms a third frustum of light and disinfects the air in the disinfection chamber. The light source is arranged so that the third frustum of light is substantially coaxial with the first frustum, and the first and third frusta diverge along a substantially same direction.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

A reference in the specification to "one embodiment" or "an embodiment" means that a particular feature, structure, characteristic, or function described in connection with the embodiment is included in at least one embodiment of the disclosure. The appearance of the phrase "in one embodiment," "in an embodiment," or the like in various places in the specification are not necessarily all referring to the same embodiment.

UV light is known to have germicidal properties and has been developed as the disinfection light source. Specifically, the mechanism by which UV light kills microorganisms is by damaging the genetic material, the deoxyribonucleic acid (DNA), of the microorganisms and wavelengths between 200-300 nm have been shown to initiate a photoreaction between adjacent pyrimidines. Hereinafter, for the purpose of illustration, it is assumed that the light sources generate UV light for disinfection, even though the light sources are able to generate light in other wavelength ranges for disinfection. Also, it is noted that the disinfection devices in the present disclosure can be applied to various air conditioning systems as well as the equipment for epidemic/pandemic events.

Figure 1:
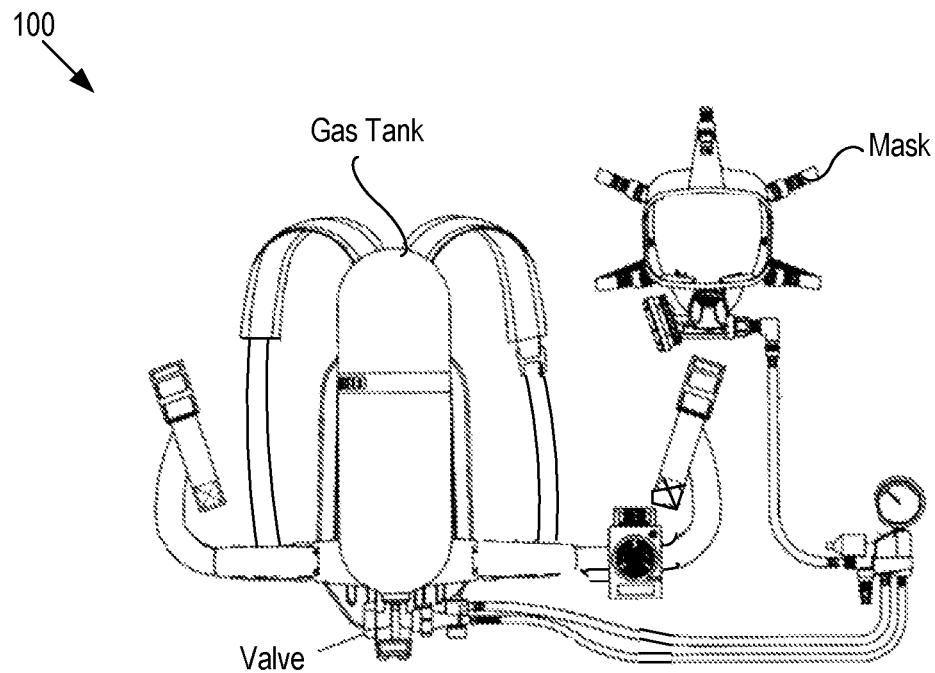
FIG. 1 shows a conventional self-contained breathing apparatus (SCBA).
Figure 2:
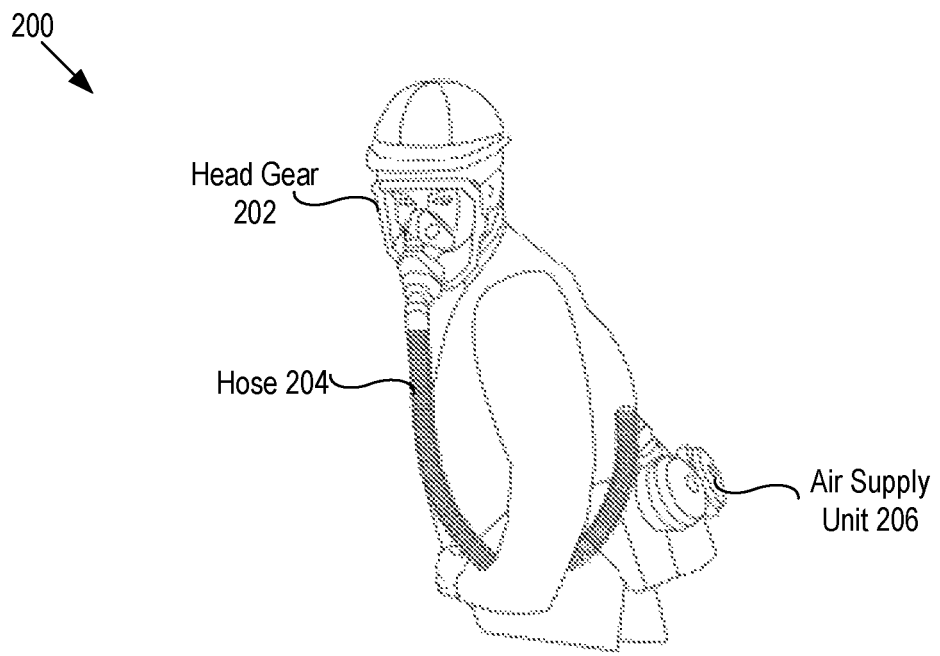
FIG. 2 shows a conventional powered, air-purifying respirator (PAPR).
Figure 3:
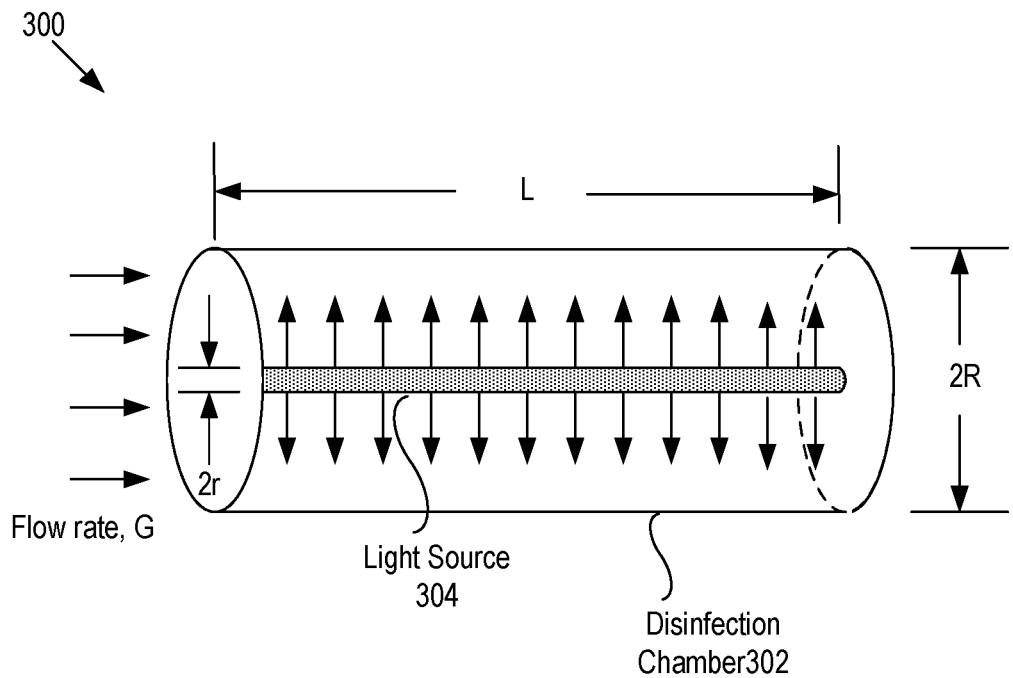
FIG. 3 shows a schematic diagram of a conventional disinfection configuration that uses a mercury (Hg) lamp.

FIG. 3 shows a schematic diagram of a conventional disinfection configuration that uses a mercury (Hg) lamp as the disinfection light source. As depicted, the conventional disinfection configuration 300 includes: a disinfection chamber 302 containing fluid to be disinfected; and a light source 304 for disinfecting the fluid in the disinfection chamber.

The light source 304 is a mercury (Hg) lamp and has the shape of a circular cylinder and is arranged along the axial direction of the disinfection chamber 302. (Hereinafter, the configuration 300 is termed as linear configuration since the light source is a linear pen lamp.) In the linear configuration 300, the average dosage of light experienced by the fluid is expressed as:

$$\mathcal{J} = \frac{P(R+r_0)}{2G}\left[\ln\frac{R}{r_0} + \sum_{n=1}^{\infty}\frac{(-\alpha)^n(R^n - r_0^n)}{n.n!}\right] \quad (1)$$

where, G, P, R, $r_0$, and $\alpha$ refer to the fluid (volumetric) flow rate, optical output power of the light source, radius of the disinfection chamber, radius of the light source, and the absorption coefficient of the light by the fluid. When $\alpha$ approaches zero, equation (1) can be simplified as:

$$\mathcal{J} = \frac{P(R+r_0)}{2G}\ln\frac{R}{r_0} \quad (2)$$

Figure 4:
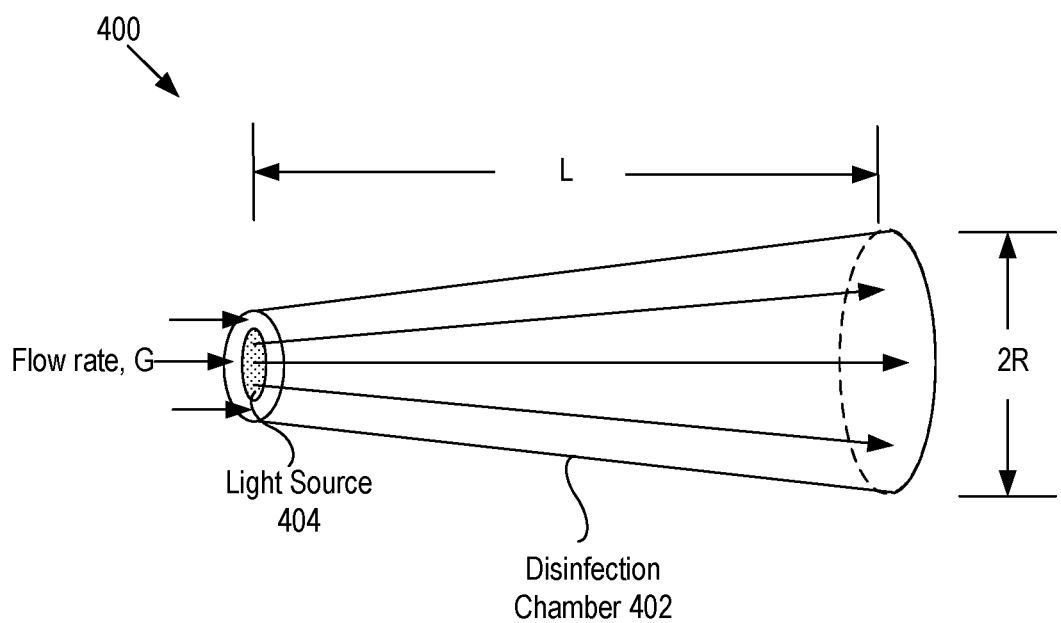
FIG. 4 shows a schematic diagram of a disinfection configuration according to embodiments of the present disclosure.

FIG. 4 shows a schematic diagram of a disinfection configuration 400 according to embodiments of the present disclosure. As depicted, the disinfection configuration 400 includes; a light source 404; and a disinfection chamber 402 that has the shape of a conical frustum and contains the fluid to be disinfected. In embodiments, the light emitted by the light source 404, which may be preferably, but not limited to, an ultraviolet light emitting diode (UV-LED), has the light pattern shape of a cone (or conical frustum), and the divergence angle (or equivalently aperture angle) of the cone is about the same as the aperture angle of the disinfection chamber 402. Hereinafter, the aperture angle of a right circular conical frustum (or a circular cone) refers to the maximum angle between any two generatrix lines of the right circular conical frustum (or a circular cone).

It is noted that, unlike the linear configuration 300 in FIG. 3, the light source 404 is located near the vertex of the disinfection chamber 402, and most of the light emitted by the light source 404 is located within the disinfection chamber 402. (Hereinafter, the configuration 400 is termed as point configuration since the light source is located near the vertex of the disinfection chamber 402.)

In the point configuration 400, the dosage of light experienced by the fluid is expressed as:

$$J = \frac{P}{\alpha G}(1 - e^{-\alpha L}) \quad (3)$$

where G, P, L and α refer to the fluid volumetric flow rate, optical output power of the light source, length of the disinfection chamber and the absorption coefficient of the light by the fluid. When α approaches zero, equation (3) can be simplified as:

$$J = \frac{PL}{G} \quad (4)$$

Figure 5:
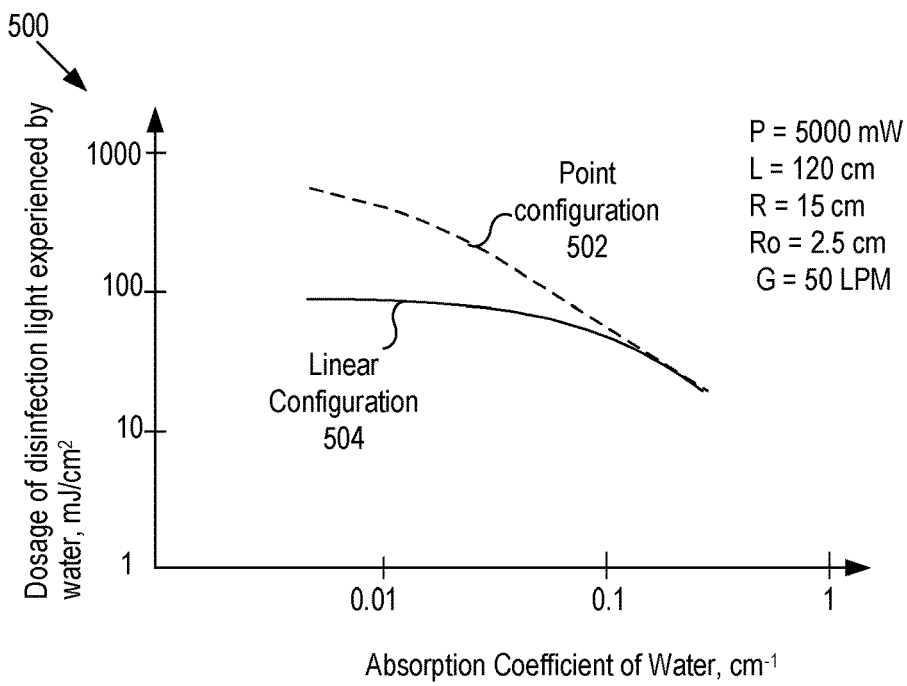
FIG. 5 shows a plot of the dosage of light experienced by the water as a function of absorption coefficient according to embodiments of the present disclosure.

To explain the effect of the absorption coefficient, α, on the dosages of the disinfection light experienced by the water in the configurations 300 and 400, equations (1) and (3) are used with the following fixed parameters: P=5000 mW, L=120 cm, R=15 cm, $r_0$=2.5 cm, and G=50 liter per minute (LPM). FIG. 5 shows a plot 500 of the dosages of light experienced by the water as functions of absorption coefficient according to embodiments of the present disclosure. In FIG. 5, the curves 502 and 504 refer to the dosages that correspond to the configurations 400 and 300, respectively. As depicted, when the absorption coefficient is less than 0.1 $cm^{-1}$, the point configuration 400 delivers much higher dosage of light to the water than the linear configuration 300. Especially, when the absorption coefficient is less than 0.01 $cm^{-1}$, the point configuration 400 shows a significant advantage over the linear configuration 300.

Figure 6:
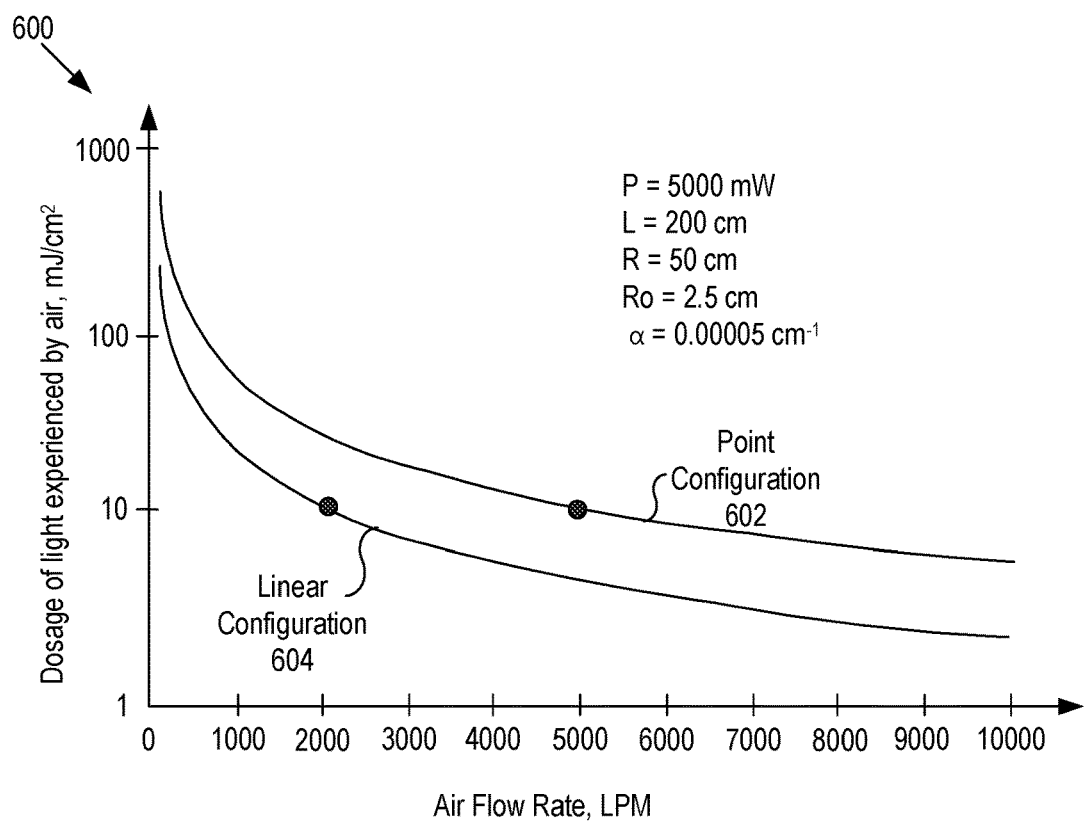
FIG. 6 shows a plot of the dosage of light experienced by the air as a function of air flow rate according to embodiments of the present disclosure.

The absorption coefficient, α, of the air in the UV wavelength range is very small. In such a case, to compare the efficiency in delivering the disinfection light to the air in the configurations 300 and 400, equations (2) and (4) (or, equations (1) and (3)) can be used with the following fixed parameters: P=5000 mW, L=200 cm, R=50 cm, $r_0$=2.5 cm, and α=0.00005 $cm^{-1}$. FIG. 6 shows a plot 600 of the dosage of the light experienced by the air as a function of air flow rate according to embodiments of the present disclosure. In FIG. 6, the curves 602 and 604 refer to the dosages that correspond to the configurations 400 and 300, respectively. As depicted, the point configuration 400 delivers higher dosage of light than the linear configuration 300.

As discussed above, the point configuration 400 can be used to disinfect air generated by an air conditioner. By way of example, for a typical room size of 30 $m^2$ with air volume of 90 $m^3$ and the air flow rate of 5000 LPM (177 CFM), the dosage of UV light required for 99.99% reduction for most microorganisms is 10 $mJ/cm^2$. In the point configuration 400 having the output power P of 5 Watt, it takes about 18 minutes to deliver this required dosage while it takes about 45 minutes in the linear configuration 300 having the same output power. As such, it can be noticed that the point configuration 400 is more effective in delivering the disinfection light to the air than the linear configuration 300.

Figure 7:
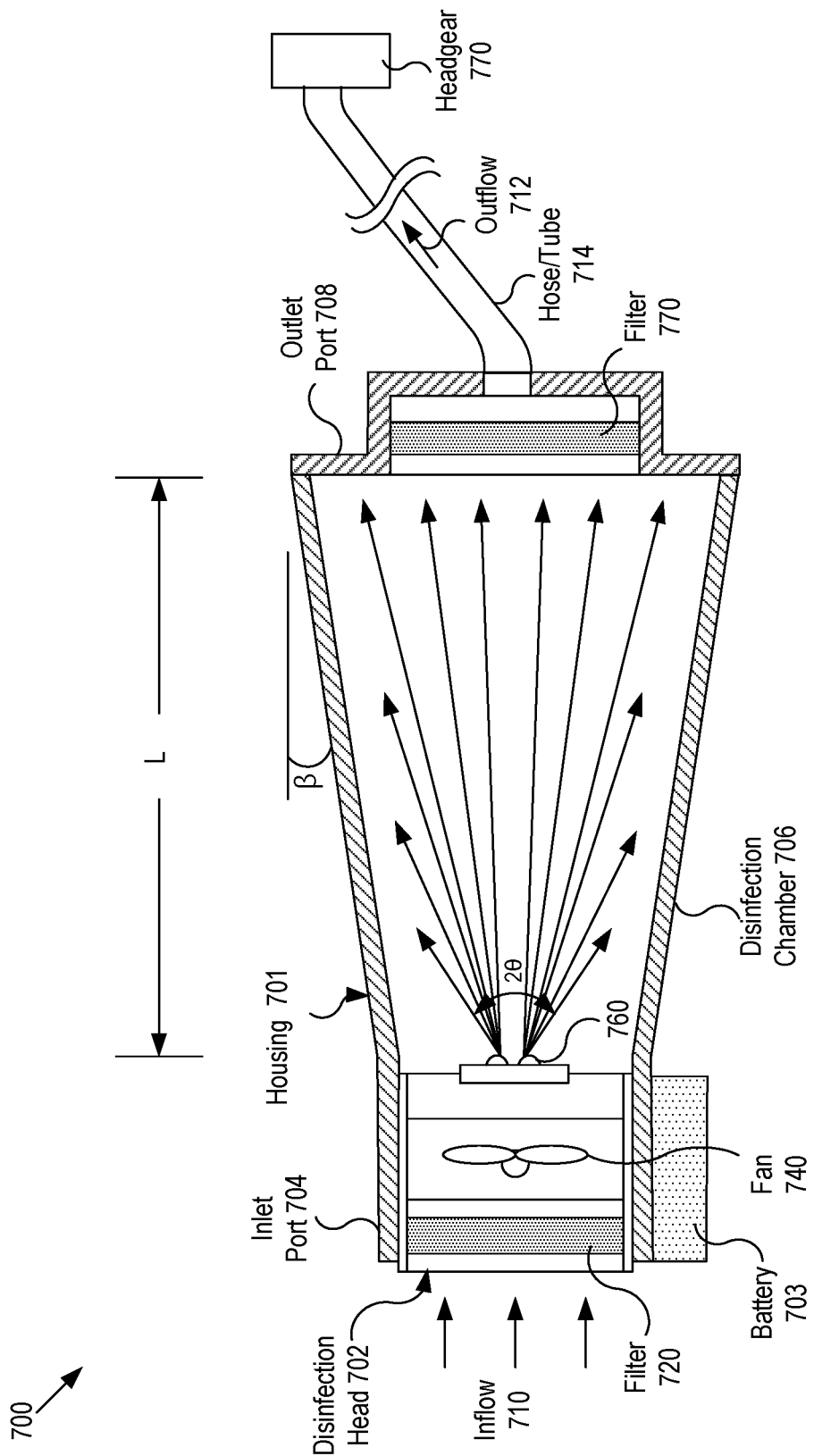
FIG. 7 shows a cross sectional view of a disinfection device according to embodiments of the present disclosure.
Figure 8:
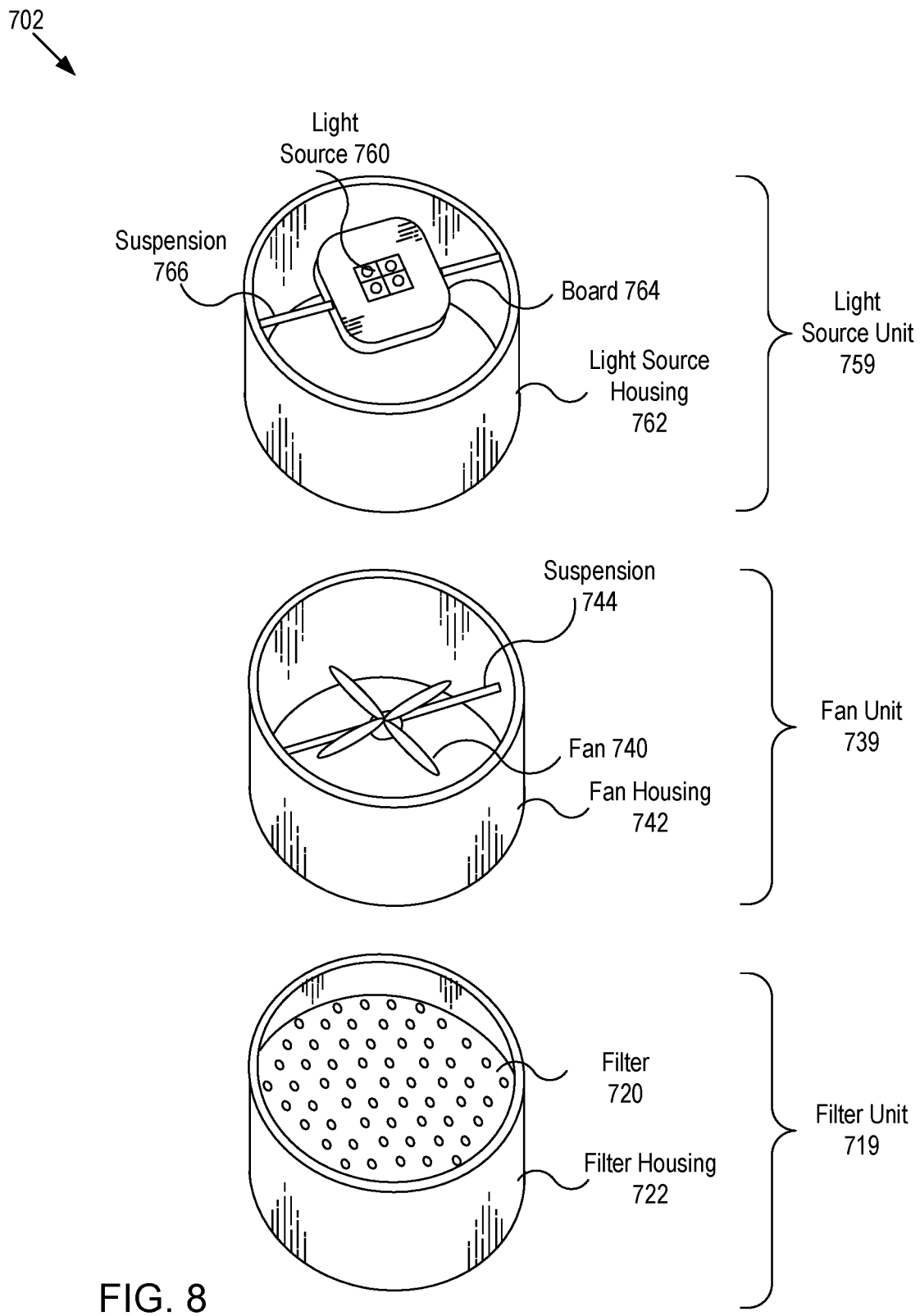
FIG. 8 shows an exploded view of a disinfection head according to embodiments of the present disclosure.

Since the point configuration 400 is more effective in delivering disinfection light dose than the linear configuration 300, in embodiments, the disinfection devices are designed to have configurations that are similar to the point configuration 400. FIG. 7 shows a cross sectional view of a disinfection device 700 according to embodiments of the present disclosure. FIG. 8 shows an exploded view of a disinfection head 702 according to embodiments of the present disclosure. As depicted, the disinfection device 700 includes: a housing 701; a disinfection head 702 mounted in the housing and configured to provide clean air; and a battery 703 for providing electrical power for the disinfection head 702. In embodiments, the housing 701 includes: an inlet port 704 for receiving the disinfection head 702; a disinfection chamber 706 in which the air is disinfected by the disinfection light; and an outlet port 708 coupled to a tube/hose 714. In embodiments, the contaminated ambient air is taken into the disinfection head 702, as indicated by the arrows 710, and exits the disinfection device 700 through the tube 714, as indicated by an arrow 712.

In embodiments, the disinfection device 700 may be used in place of the conventional PAPR 200, more specifically the air supply unit 206 of the PAPR 200. For instance, a headgear 770 (such as mask or hood), which is similar to the headgear 202, may be coupled to the disinfection device 700 via the hose/tube 714 to form a portable disinfection device, where the disinfection device 700 is in fluid communication with the headgear 770 via the hose/tube 714.

In embodiments, the disinfection head 702 includes: a filter unit 719 for filtering contaminants, such as pollution or pathogenic microorganisms, in the air; a fan unit 739 for taking the contaminated ambient air into the filter unit 719 so that the contaminated air passes through the filter unit; and a light source unit 759 for providing disinfection light to the air that is filtered by the filter unit 719.

In embodiments, the filter unit 719 includes: a filter housing 722; and an inlet filter (or shortly filter) 720 that is formed of fibrous or porous materials and filters contaminants, such as dust, pollen, mold, and bacteria, and droplets containing the virus from the air. In embodiments, only the filter 720 can be replaced or the entire filter unit 719 can be replaced for maintenance. In embodiments, the filter housing 722 is secured to the inlet port 704 of the housing 701 by a suitable fastening mechanism, such as threads that are formed on the inner surface of the inlet port and the outer surface of the filter housing.

In embodiments, the fan unit 739 includes: a fan 740 having a motor; a fan housing 742; and one or more suspensions/rods 744 for securing the fan to the fan housing. In embodiments, the suspensions 744 include a wire for providing electrical power for the fan 740 from the battery 703. In embodiments, the fan 740 takes the contaminated ambient air into the filter unit 719 to thereby pressurize the disinfection chamber 706 and hose/tube 714 and to cool down the light source 760 with the air flow. In embodiments, the fan housing 742 is secured to the inlet port 704 of the housing 701 by a suitable fastening mechanism, such as threads that are formed on the inner surface of the inlet port and the outer surface of the fan housing.

In embodiments, the light source unit 759 includes: a light source 760; a board 764 having an electrical circuit for controlling the light 760, where the light source 760 is mounted on the board; a light source housing 762; and one or more suspensions/rods 766 for securing the board 764 to the light source housing. In embodiments, the board 764, which may be a printed circuit board (PCB), is made mainly of aluminum or copper, and includes electrical circuits for controlling the electrical power to the light source 760. In embodiments, the light source 760 includes one or more UV-LEDs. In embodiments, the suspensions 766 include a wire for providing electrical power for the board 764 from the battery 703. In embodiments, the light source housing 762 is secured to the inlet port 704 of the housing 701 by a suitable fastening mechanism, such as threads that are formed on the inner surface of the inlet port and the outer surface of the light source housing.

In embodiments, the filter unit 719, fan unit 739 and the light source unit 759 are separated from each other so that they can be replaced individually. During operation, the filter unit 719, fan unit 739 and the light source unit 759 are air-tightly secured to the inlet port 704 so that the ambient air enters the disinfection chamber 706 only through the filter 720. In alternative embodiments, the filter housing 722, fan housing 742 and the light source housing 762 are formed in one monolithic body so that the filter 720, fan 740 and light source 760 are individually replaced from the disinfection head 702.

In embodiments, the inlet port 704 and disinfection chamber 706 are formed in one monolithic body. In alternative embodiments, to allow for an easy access to the disinfection head 702, the inlet port 704 and disinfection chamber 706 are formed of two separate bodies, and detachably secured to each other via a sealing mechanism, such as O-ring.

In embodiments, the outlet port 708 may include an outlet filter (or shortly filter) 770, where any contaminant in the disinfected air is filtered by the filter 770 before the air exits the outlet port. In embodiments, the outlet port 708 is detachably secured to the housing 701 so that the filter 770 can be accessed and replaced.

In embodiments, the disinfection chamber 706 has a shape of a first frustum that has an aperture angle (or, equivalently divergence angle) $2\beta$. Similarly, in embodiments, the light emitted by the light source 760 forms a second frustum (or a cone) of light (or, simply, a light frustum). The aperture angle (or, equivalently divergence angle) of the second frustum of light can also be called as the light source beam angle, or viewing angle as it is commonly referred to, measures the usable light emitted from an LED source. In this specification, it is defined as the angle at which 50% of the peak light intensity is reached on either side of the origin (light source). For example, if an LED is measured to have 50% peak intensity at 15° off the origin, it's viewing angle (aperture angle) would be 30°. So, it is clear that the second frustum (of light) contains most of the light, not all of the light, emitted by the light source. Light source 760 is designed and arranged so that the second frustum of light is coaxial with the first frustum (of chamber), and the first and second frusta diverge along the same direction.

Optionally, the aperture angle (or, equivalently divergence angle) of the second frustum of light, $2\theta$, is close to the aperture angle, $2\beta$, of the first frustum of disinfection chamber 706. Stated differently, the following equation is satisfied:

$$2\theta = 2\beta \pm 2\varepsilon \quad (5)$$

where $\varepsilon$ is less than, for example, 15 degrees, or less than 10 degrees, or less than 5 degrees.

It is noted that, if the aperture angle, $2\theta$, of the second frustum of light (light frustum) is larger than the aperture angle, $2\beta$, of the first frustum of the disinfection chamber 706, some portion of the light in the light frustum impinges on the inner wall of the disinfection chamber 706, decreasing the minimum path length of the light. Likewise, if the aperture angle, $2\theta$, of the light frustum is smaller than the aperture angle, $2\beta$, of the first frustum of the disinfection chamber 706, the air located outside the light frustum in the disinfection chamber may not be properly disinfected, i.e., the disinfection efficiency may decrease. Thus, by making the aperture angle, $2\theta$, of the light frustum be close to the aperture angle, $2\beta$, of the first frustum of the disinfection chamber 706 (i.e., making the angle $2\varepsilon$ as small as possible), both the path length of the light in the disinfection chamber 706 and the disinfection efficiency are maximized. When the angle $2\varepsilon$ approaches zero, the lateral surface of the light frustum substantially coincides with an inner lateral surface of disinfection chamber 706 while an entire portion of a space defined by the disinfection chamber 706 is substantially located within the light frustum.

In embodiments, since disinfection chamber 706 has substantially the same aperture angle as the light frustum, most of the light beam in the disinfection chamber 706 is absorbed by the fluid without being reflected on the inner lateral surface of the disinfection chamber, i.e., the light beams fulfill the volume defined by the disinfection chamber 706 with as little light impinging on the chamber sidewall as possible. In embodiments, the inner sidewall of the disinfection chamber 706 is coated with material that reflects the light impinging thereon. For example, the inner sidewall of disinfection chamber 706 can be coated with thin (e.g. 100-1000 nm thick) aluminum layer which has germicidal ultraviolet light reflectivity of 90% or above, or it can be coated with micro or sub-micro porous Polytetrafluoroethylene (PTFE) with nominal thickness greater than 1 millimeter (mm), for example, 3 mm, possessing UV reflectivity above 90%, for example, 95%, or 99%. When the inner sidewall of disinfection chamber 706 is highly UV reflective, the aperture angle, $2\theta$, of the light frustum is preferably larger than the aperture angle, $2\beta$, of the disinfection chamber 706.

In embodiments, the human respiratory minute volume (G) usually is 6-10 LPM (or, equivalently air flow of 100-167 ml/s). To achieve 99.99% reduction for most microorganisms, the dosage, J, of UVC light (260-280 nm) experienced by the air needs to be 10 mJ/cm$^2$ or above. By way of example, the light source 760 is assumed to be a UV-LED that emits UVC light with an aperture angle of 30 degrees, where the disinfection chamber 706 is assumed to have the same aperture angle of 30 degrees. Since the UVC light absorption coefficient by clean air is in the order of $10^{-6}$ cm$^{-1}$, equation (4) can be used to determine the length L of the disinfection chamber 706 to deliver the required dosage of light for a given output power P of the light source. For example, assuming G=10 LPM, J=40 mJ/cm$^2$, and P=400 mW, the require length L of the disinfection chamber 706 is 16.7 cm. In another example, assuming G=10 LPM, J=10 mJ/cm$^2$, and P=100 mW, the require length L of the disinfection chamber 706 is also 16.7 cm. Stated differently, the disinfection device 700 is able to deliver the dosage of 10-40 mJ/cm$^2$ when the output power P of the light source is 100-400 mW and the length of the disinfection chamber 706 is 16.7 cm.

In embodiments, as a portable respiratory device, the disinfection device 700 is able to effectively treat airborne microbes using a light source that can generate UVC optical output of 100 mW and above, as discussed above. Also, the required dimension of the housing 701 is in the range of 10-30 cm, preferably 15-20 cm, which enables the disinfection device 700 to be of small size and light weight. Moreover, in embodiments, the light source unit (such as 759) and the fan unit (such as 739) consume small amount of electricity, around 5-10 W, allowing them to be powered by a portable battery 703, such as a lithium ion battery of 10000 mAh, that can last for 4-7 hours per charge. The long operation time and easy replacement of battery 703 allows disinfection device 700 to be used continuously during epidemic/pandemic events. In embodiments, the disinfection head 702 can be readily replaced, significantly reducing the effort and cost for maintenance of the disinfection device 700.

Figure 9:
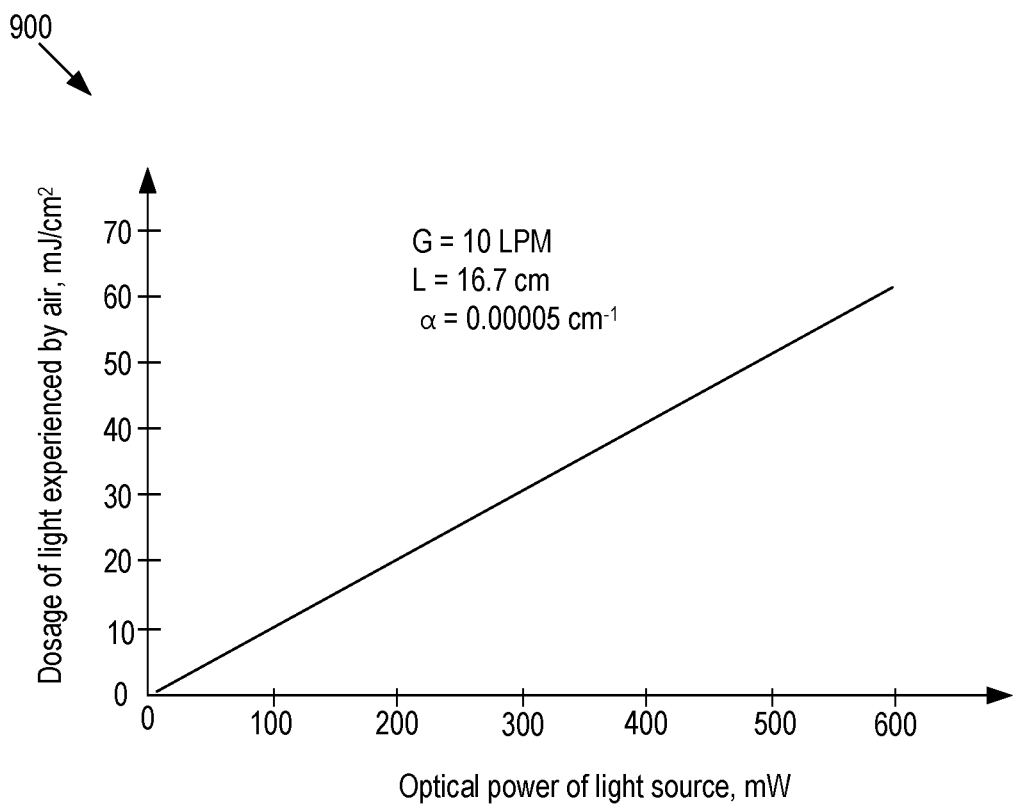
FIG. 9 shows a plot of the dosage of light experienced by the air as a function of the output power of a light source according to embodiments of the present disclosure.

FIG. 9 shows a plot 900 of the dosage of light experienced by the air as a function of the output power of a light source according to embodiments of the present disclosure. As depicted, assuming that the parameters in equation (4) have the following values: G=10 LPM, L=17 cm, and α=0.00005 cm$^{-1}$, the dosage of light experienced by the air is proportional to the output power of the light source 760. In the plot 900, it can be noticed that, when the output power of the light source 760 is 100 mW or above, the effective disinfection (i.e., 99.99% reduction for most microorganisms) can be obtained.

Figure 10A:
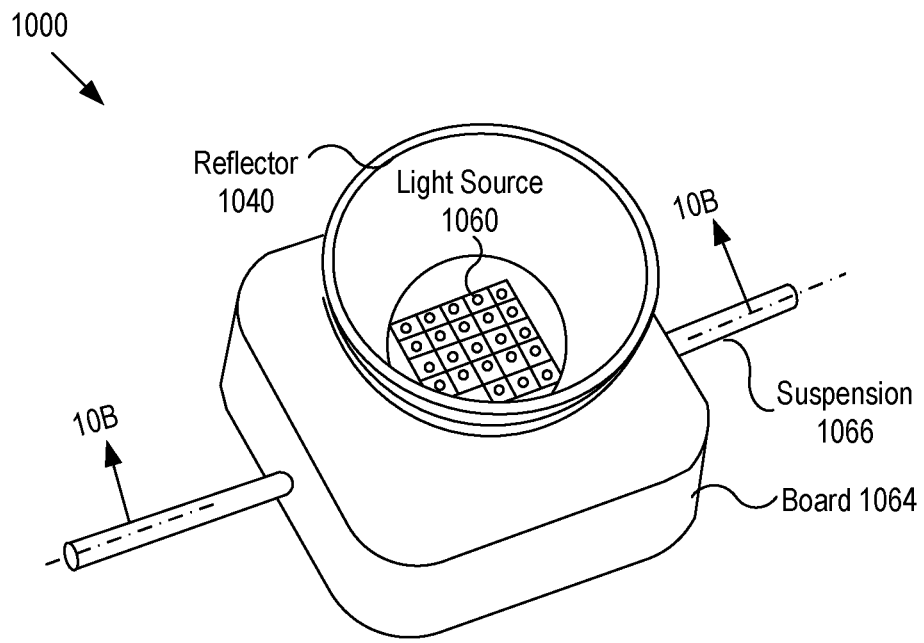
FIG. 10A shows a perspective view of a light source according to embodiments of the present disclosure.
Figure 10B:
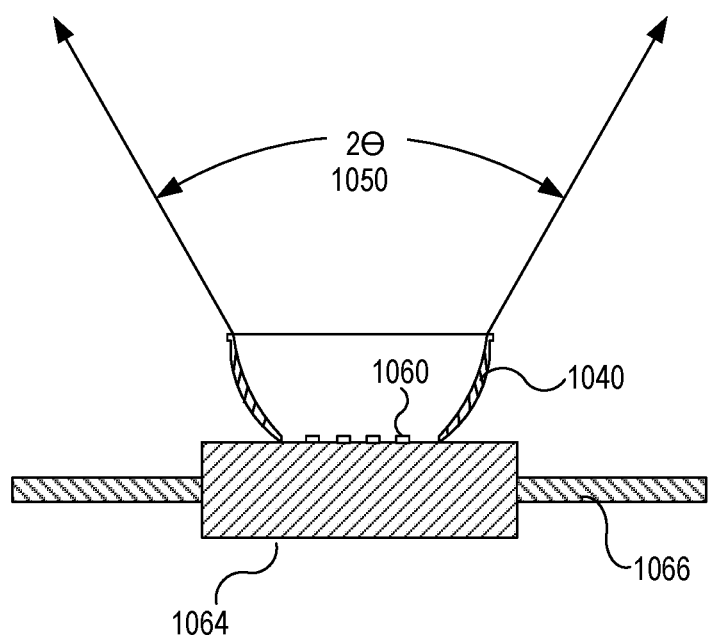
FIG. 10B shows a cross sectional view of the light source in FIG. 10A, taken along a line 10B-10B, according to embodiments of the present disclosure.

FIG. 10A shows a perspective view of a light source according to embodiments of the present disclosure. FIG. 10B shows a cross sectional view of the light source, taken along a line 10B-10B, according to embodiments of the present disclosure. As depicted, the light source 1060, board 1064 and suspension/rod 1066 are similar to their counterparts in FIG. 8, and a reflector 1040 is mounted on the board 1064. In embodiments, the reflector 1040 has a shape of a curved-cone (or bell) or a paraboloid so that light leaving the reflector 1040 may have the shape of a right circular frustum with an aperture angle (or cone angle), 2θ, 1050.

Figure 11:
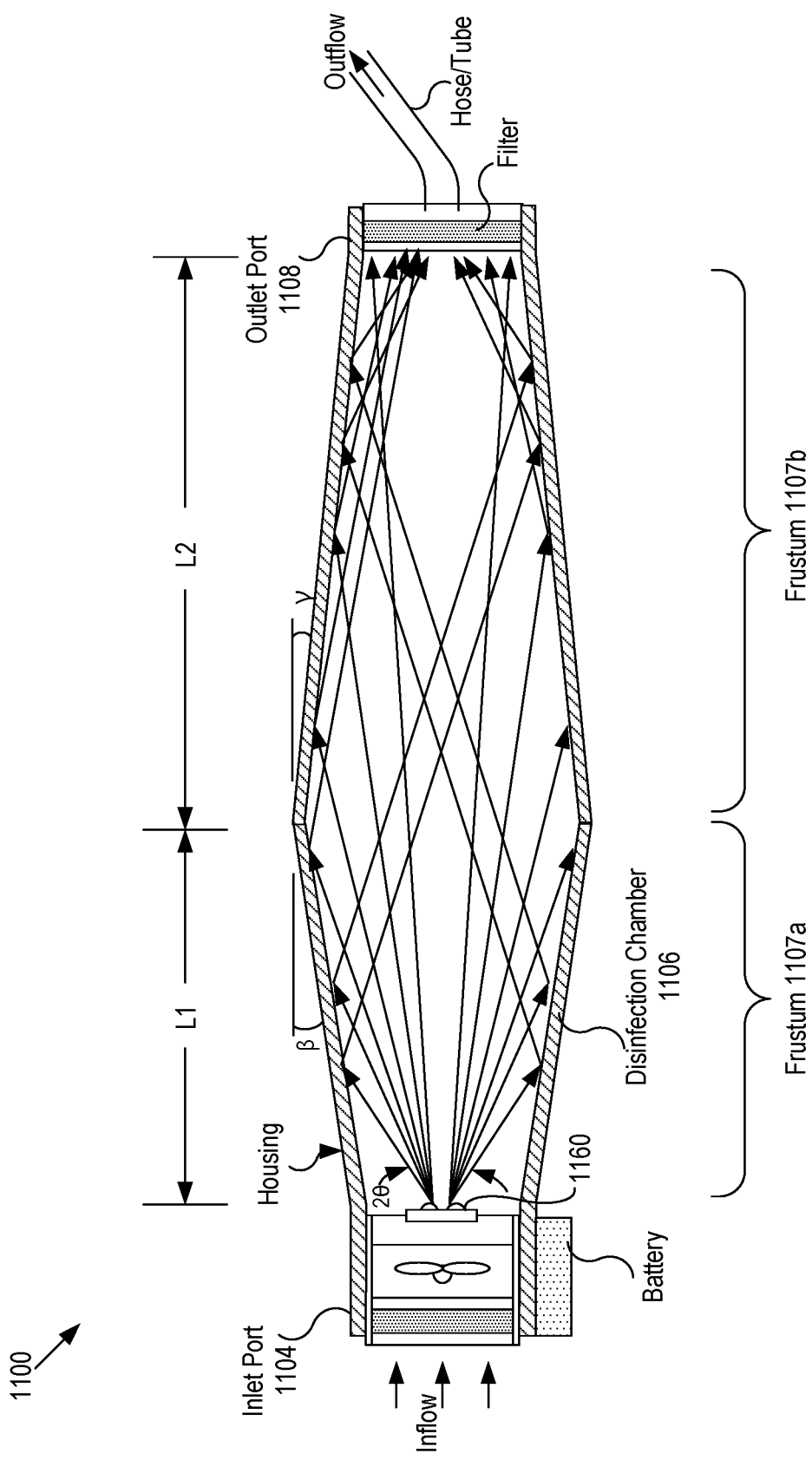
FIG. 11 shows a cross sectional view of a disinfection device according to embodiments of the present disclosure.

FIG. 11 shows a cross sectional view of a disinfection device 1100 according to embodiments of the present disclosure. As depicted, the disinfection device 1100 is similar to the disinfection device 700, with the difference that the disinfection chamber 1106 includes two conical frustum shells 1107a and 1107b. In embodiments, the two conical frustum shells 1107a and 1107b have the same base diameter, the inlet port 1104 is disposed in the vertex side (or, equivalently top side) of the conical frustum shell 1107a and the outlet port 1108 is disposed in the vertex side (or, equivalently top side) of the conical frustum shell 1107b.

In embodiments, the light emitted by the light source 760 has the shape of a third frustum (or, cone), where the aperture angle of the third frustum is 2θ. The aperture angles of the two frusta 1107a and 1107b are respectively 2β and 2γ, where the three aperture angles 2θ, 2β and 2γ satisfy one of the following equations:

$$2\theta \geq 2\beta \geq 2\gamma \quad (6)$$

$$2\theta \geq 2\beta, \text{ and } 2\gamma = 2\beta \pm 2\epsilon \quad (7)$$

where, ε is less than 10 degrees. In embodiments, the light source is arranged so that a lateral surface of the third frustum of the disinfection light is substantially identical to an inner lateral surface of the first frustum shell. Also, the light source is disposed near a top of the first frustum shell so that an entire portion of a space defined by the first frustum shell is located within the third frustum of the disinfection light.

Figure 12:
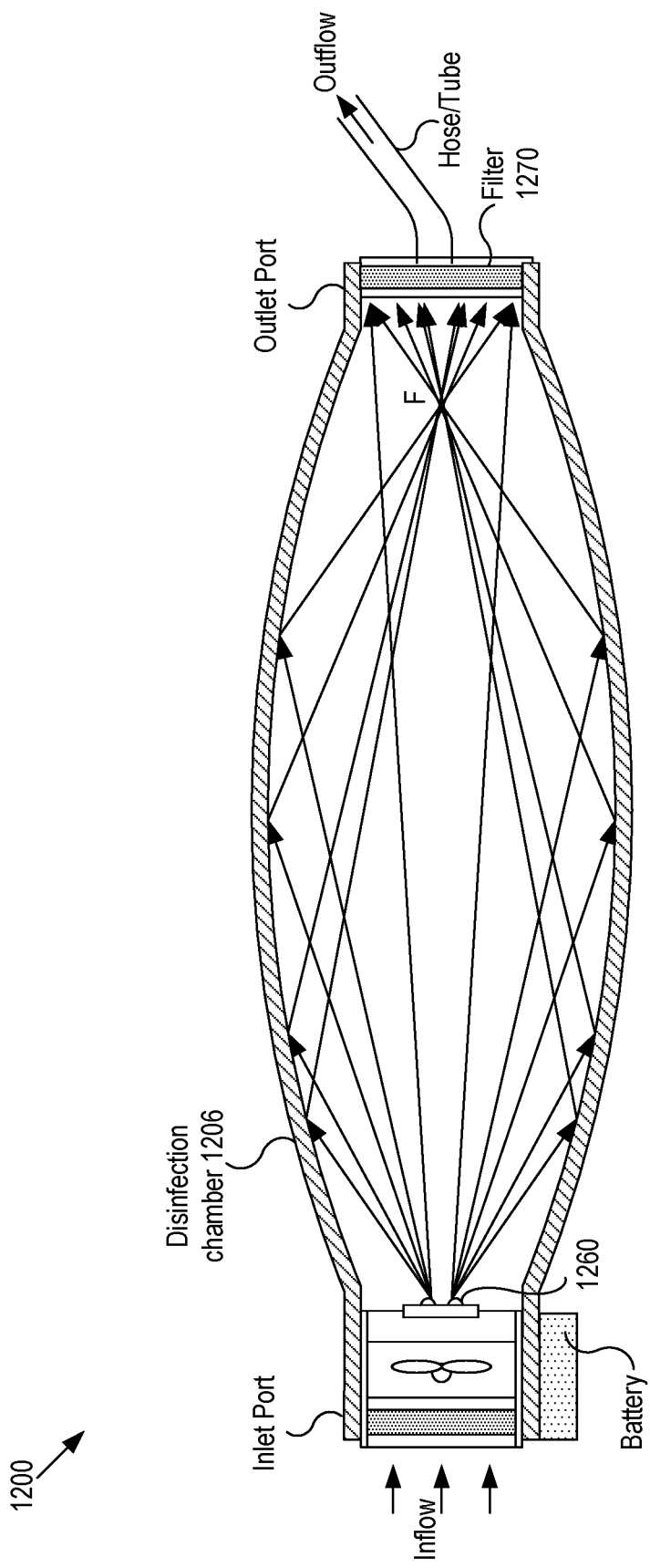
FIG. 12 shows a cross sectional view of a disinfection device according to embodiments of the present disclosure.

FIG. 12 shows a cross sectional view of a disinfection device 1200 according to embodiments of the present disclosure. As depicted, the disinfection device 1200 is similar to the disinfection device 700, with the difference that the disinfection chamber 1206 has a shape of a truncated ellipsoidal shell (such as truncated spheroidal shell). In embodiments, the light source 1260 is located on or in the vicinity of one of the two focal points of the truncated ellipsoid, while the filter 1270 on the outlet side is located slightly away from the other focal point (or equivalently focus), F, of the truncated ellipsoid so that the light is not focused on the filter 1270. In embodiments, the light source 1260 is located on a plane where a focal point of the truncated ellipsoid is located. For instance, the light source 1260 includes multiple light emitting elements, such as LEDs, where the light emitting elements are disposed on a plane where a focal point of the truncated ellipsoid is located.

In embodiments, the rotational axis of the blades of the fan is parallel to the axis that passes through the two focal points of the truncated ellipsoid. In embodiments, the rotational axis of the blades of the fan passes through at least one of the two focal points of the truncated ellipsoid For the embodiments shown in FIGS. 11 and 12, a great portion of light emitted by light sources 1160 and 1260 is experienced one or two reflections by the disinfection chamber inner sidewall, therefore, the inner sidewall is preferably coated with thin (e.g. 100-1000 nm thick) aluminum layer which has germicidal ultraviolet light reflectivity of 90% or above, or it can be coated with micro or sub-micro porous Polytetrafluoroethylene (PTFE) with nominal thickness greater than 1 millimeter (mm), for example, 3 mm, possessing UV reflectivity above 90%, for example, 95%, or 99%.

Figure 13:
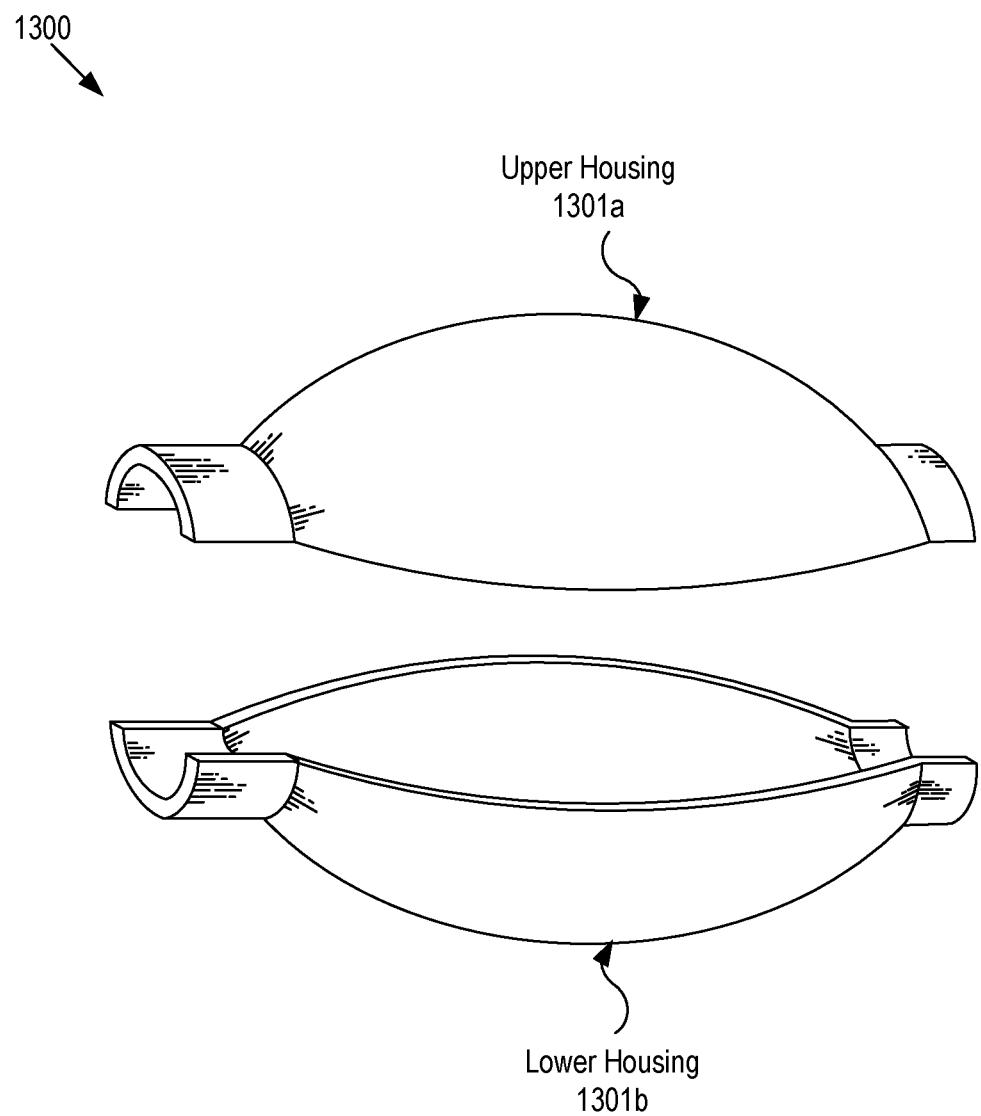
FIG. 13 shows a perspective view of a housing according to embodiments of the present disclosure.

In embodiments, each of the disinfection chambers in FIGS. 4-12 can be formed of a monolithic body, or can be formed of two or more parts. FIG. 13 shows a cross sectional view of a housing 1300 according to embodiments of the present disclosure. As depicted, the housing 1300 includes: the upper housing 1301a and the lower housing 1031b, where the upper and lower housings are detachably joined to form an air tight chamber via a suitable sealing mechanism, such as O-ring.

In embodiments, the inner surface of the housing 1300 may be coated with material that reflects the disinfection light. For instance, the light source is a UVC-LED and the coating is formed of aluminum or polytetrafluoroethylene. In embodiments, when the housing 1300 is made of two parts, coating of the inner surface is easier to be realized.

Figure 14:
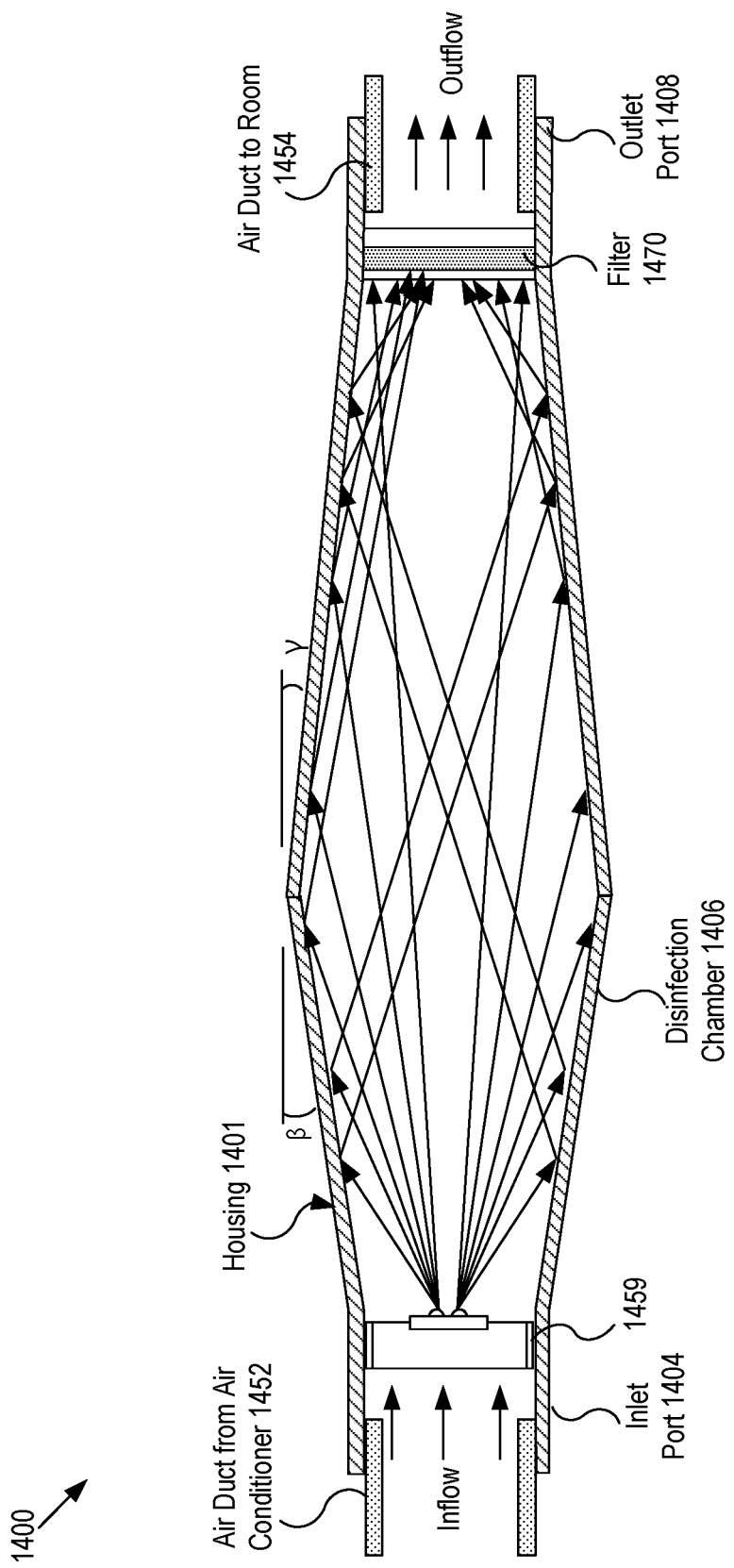
FIG. 14 shows a cross sectional view of a disinfection device according to embodiments of the present disclosure.

As discussed above, in embodiments, the disinfection devices in FIGS. 7-13 may be used as portable respiratory device. For instance, the disinfection devices in FIGS. 7-13 may be used in place of the air supply unit 206. In embodiments, the disinfection devices in FIGS. 7-13 may be also applied to air conditioning systems. More specifically, the disinfection devices in FIGS. 7-13 may be used to disinfect the contaminants in the air that is cooled by an air conditioner. FIG. 14 shows a cross sectional view of a disinfection device according to embodiments of the present disclosure. As depicted, the disinfection device 1400 includes: a housing 1401 having an inlet port 1404, a disinfection chamber 1406, and an outlet port 1408; a light source unit 1459 mounted in the inlet port; and an outlet filter 1470 mounted in the outlet port 1408. In embodiments, the disinfection chamber 1406 is similar to the disinfection chamber 1106 in FIG. 11. It is noted that the disinfection chamber 1406 may have the similar shapes as the disinfection chambers in FIGS. 7 and 12-13.

In embodiments, the light source unit 1459 is similar to the light source unit 759 in FIG. 8, with the difference that an AC power supply provides the electrical power to the light source unit 1459.

In embodiments, the inlet port 1404 is coupled to an air duct 1452 from an air conditioner that is able to cool down the air, filter the air, and generate air flow in the air duct 1452. As such, unlike the disinfection head 702, the disinfection device 1400 does not have a fan or an inlet filter. In embodiments, the outlet port 1408 is coupled to an air duct 1454 to a room so that the disinfected air flows into the room. In embodiments, the outlet filter 1470 is optional and may be replaced by a light absorber that prevents the disinfection light from travelling through the air duct to the room. In embodiments, the aperture angles $2\theta$, $2\beta$ and $2\gamma$ may satisfy the equations (6) or (7).

Figure 15:
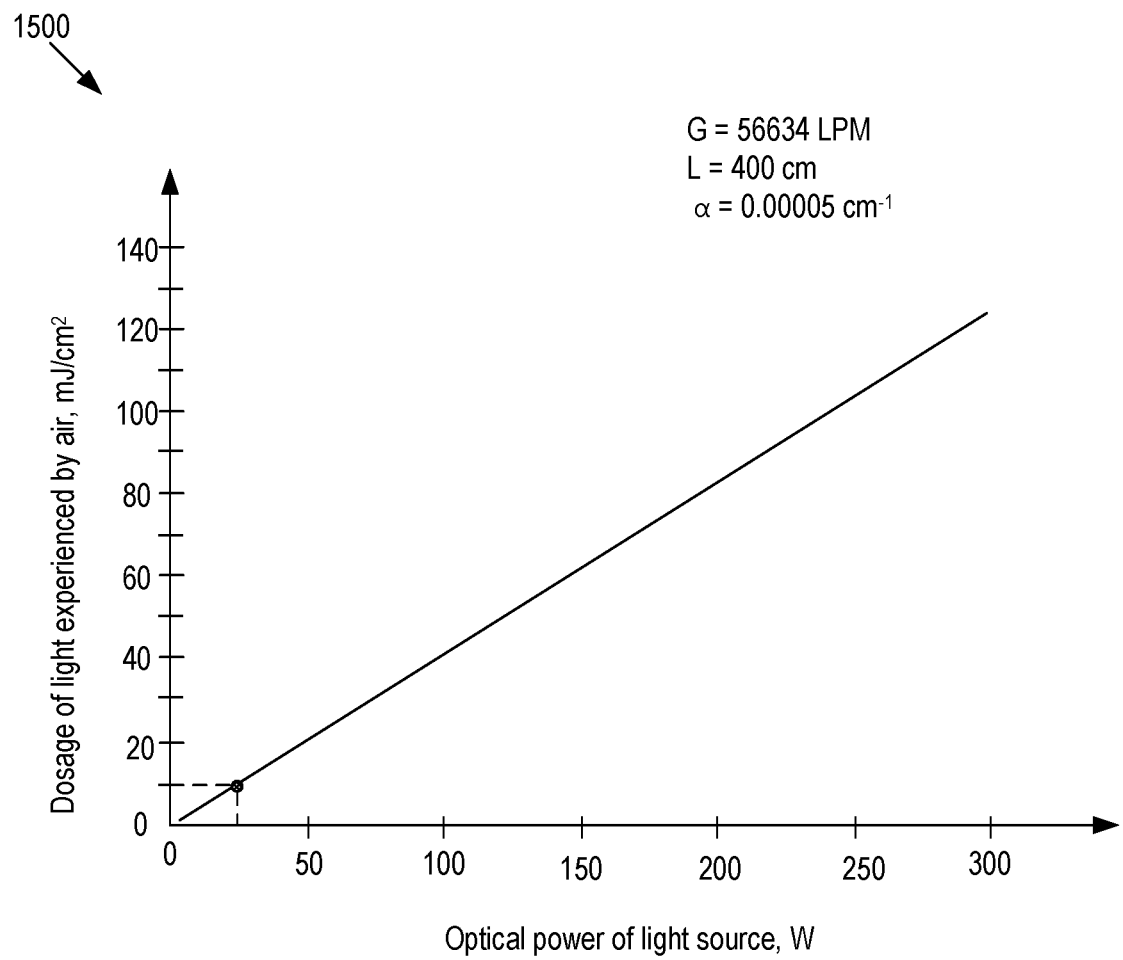
FIG. 15 shows a plot of the dosage of light experienced by the air as a function of the output power of a light source according to embodiments of the present disclosure.

By way of example, for a typical home having the size of 3000 ft$^2$, the typical air flow rate, G, from an AC is about 57000 LPM (~2000 CFM). Assuming that the length, L, of the disinfection chamber 1406 is 400 cm and the absorption coefficient $\alpha$ of the air in the UVC range is 0.00005 cm$^{-1}$, equation (4) may be used to calculate the dosage of UVC light experienced by the air as a function of the output power of the light source unit 1459. FIG. 15 shows a plot 1500 of the dosage of light experienced by the air as a function of the output power of a light source according to embodiments of the present disclosure. As shown in FIG. 15, it can be noticed that, when the output power of the light source unit 1459 is 25 W or above, the effective disinfection (i.e., 99.99% reduction for most microorganisms, or equivalently dosage of 10 mJ/cm$^2$ or higher) can be obtained.

In FIGS. 11-14, the inlet port (e.g. 1404), disinfection chamber (e.g. 1406) and outlet port (e.g. 1408) are formed in one monolithic body. In alternative embodiments, the inlet port, disinfection chamber and outlet port are formed of three separate bodies and detachably secured to each other via suitable sealing mechanism, such as O-rings, allowing for each access to the disinfection head and inner surface of the disinfection chamber.

Figure 16B:
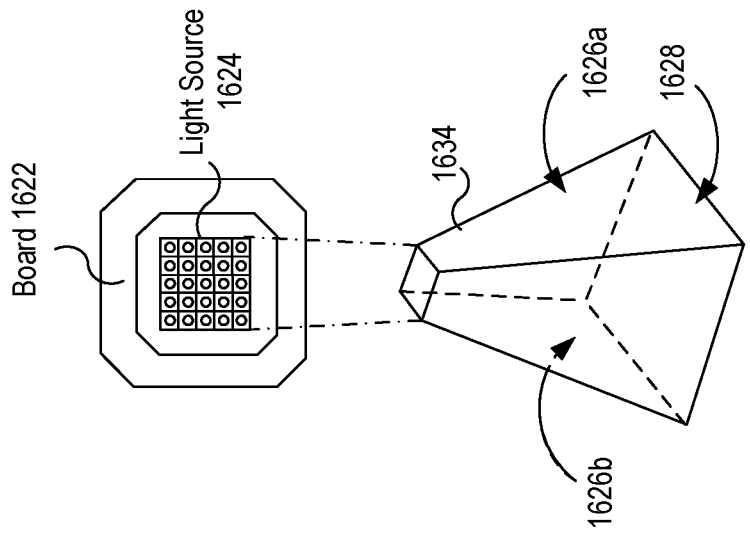
FIG. 16B shows a top view of a light source and a perspective view of a disinfection light frustum according to embodiments of the present disclosure.
Figure 16A:
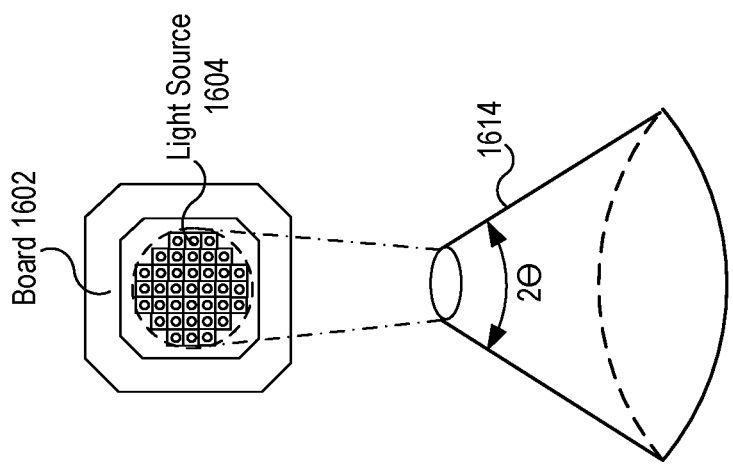
FIG. 16A shows a top view of a light source and a perspective view of a disinfection light frustum according to embodiments of the present disclosure.

FIG. 16A shows a top view of a light source 1604 and a perspective view of a disinfection light frustum 1614 generated by the light source 1604 according to embodiments of the present disclosure. In embodiments, the light source 1604, which is mounted on a board 1602, may be used as the light source 760. As depicted, the light source 1604 includes a plurality of LEDS that are arranged in a substantially circular array pattern, where the dimension of the light source 1604 may be so large that the light source may not be considered as a point light source. In alternative embodiments, the light source 1604 includes a small number of LEDS so that the light source 1604 may be considered as a point light source.

FIG. 16B shows a top view of a light source 1624 and a perspective view of a disinfection light frustum 1634 generated by the light source 1624 according to embodiments of the present disclosure. In embodiments, the light source 1624, which is mounted on a board 1622, is used as the light source light source 760. As depicted, the light source 1624 includes a plurality of LEDS that are arranged in a substantially rectangular array pattern and the light frustum 1634 has a shape of a rectangular pyramid. In such a case, the aperture angle of the light frustum 1634 is defined as the angle between two opposite lateral sides 1626a and 1626b.

In embodiments, the LEDs of the light source may be arranged such that the base 1628 of the light frustum can have various shapes, such as circle, oval, rectangle, triangle or polygon. Also, a reflector, which is similar to the reflector 1040, may be mounted on the board (such as 1602, 1622), and the shape of the reflector may be changed so as to change the shape of the light frustum. For instance, a reflector having a rectangular pyramid shape can be used to generate a light frustum having a rectangular pyramid shape. It is noted that the disinfection chamber 706 (and 1107a, 1107b) may be changed to have a similar shape as the corresponding light frustum. For instance, the disinfection chamber 706 has a rectangular pyramid shape if the light frustum has a rectangular pyramid shape 1634.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. An air disinfection device, comprising:
a housing comprising an inlet port for taking air therethrough and a disinfection chamber that includes a shell in a shape of a truncated ellipsoid;
a disinfection head disposed in the inlet port and comprising:
a light source for generating disinfection light that disinfects the air in the disinfection chamber;
wherein the light source is located substantially on a plane where a first focal point of the truncated ellipsoid is located, the plane is perpendicular to an axis of the disinfection chamber and the light source emits disinfection light in a direction along the axis of the disinfection chamber.

2. The air disinfection device of claim 1, wherein the disinfection head further comprises a fan for taking the air through the inlet port to the disinfection chamber and a filter for filtering the air, the air disinfection device further comprising:
a power source electrically coupled to the disinfection head and configured to provide electrical power for the disinfection head.

3. The air disinfection device of claim 2, wherein the fan is disposed upstream of the light source and having a plurality of rotating blades and wherein a rotational axis of the plurality of rotating blades being parallel to the axis of the disinfection housing that passes through the first focal point and a second focal point of the truncated ellipsoid.

4. The air disinfection device of claim 1, wherein the housing further comprises an outlet port through which the air disinfected by the light source exits the housing, the outlet port being disposed on a side of a second focal point of the truncated ellipsoid.

5. The air disinfection device of claim 4, further comprising:
a headgear; and
a hose having one end secured to the headgear and the other end to the outlet port of the housing so that the headgear is in fluid communication with the housing.

6. The air disinfection device of claim 4, further comprising:
a filter disposed in the outlet port and configured to filter the air that exits the housing,
wherein the filter is spaced apart from the second focal point so that the disinfection light is not focused on the filter.

7. The air disinfection device of claim 1, wherein the disinfection chamber includes two truncated half-ellipsoidal shells that are detachably joined to each other by a sealing mechanism.

8. The air disinfection device of claim 1, wherein an inner surface of the disinfection chamber is coated with a material that reflects the disinfection light.

9. The air disinfection device of claim 8, wherein the material is at least one of aluminum and polytetrafluoroethylene (PTFE).

10. The air disinfection device of claim 1, wherein the disinfection light emitted from the light source is focused on a second focal point of the truncated ellipsoid after being reflected one or more times from an inner surface of the disinfection chamber.

11. The air disinfection device of claim 1, further comprising a battery, wherein the disinfection head comprises a fan for taking the air through the inlet port to the disinfection chamber, and the battery is as a power source for the light source and the fan.

* * * * *